United States Patent
Surti

(10) Patent No.: US 7,520,886 B2
(45) Date of Patent: Apr. 21, 2009

(54) ENDOSCOPIC CUTTING DEVICE

(75) Inventor: Vihar C. Surti, Winston-Salem, NC (US)

(73) Assignee: Wilson-Cook Medical Inc., Winston-Salem, NC (US)

( * ) Notice: Subject to any disclaimer, the term of this patent is extended or adjusted under 35 U.S.C. 154(b) by 0 days.

(21) Appl. No.: 11/341,298

(22) Filed: Jan. 27, 2006

(65) Prior Publication Data

US 2006/0184187 A1 Aug. 17, 2006

Related U.S. Application Data

(60) Provisional application No. 60/647,517, filed on Jan. 27, 2005.

(51) Int. Cl.
*A61B 17/32* (2006.01)
*A61B 17/22* (2006.01)
*B26B 13/00* (2006.01)
*B26B 17/00* (2006.01)

(52) U.S. Cl. .................. 606/170; 606/159; 30/91.2; 30/188; 30/249; 30/261; 30/287

(58) Field of Classification Search ................ 606/170, 606/159, 167, 178, 180; 112/169; 30/91.2, 30/287, 131, 145, 173, 188, 194, 212, 244, 30/249, 261

See application file for complete search history.

(56) References Cited

U.S. PATENT DOCUMENTS

| | | | |
|---|---|---|---|
| 4,963,147 A | * | 10/1990 | Agee et al. ............... 606/170 |
| 5,201,759 A | * | 4/1993 | Ferzli ...................... 606/207 |
| 5,304,190 A | | 4/1994 | Reckelhoff et al. |
| 5,772,676 A | | 6/1998 | Cuschieri et al. |
| 6,193,715 B1 | | 2/2001 | Wrublewski et al. |
| 6,616,661 B2 | * | 9/2003 | Wellman et al. ............ 606/50 |
| 2002/0022788 A1 | * | 2/2002 | Corvi et al. ............... 600/564 |
| 2004/0059351 A1 | * | 3/2004 | Eigler et al. ............... 606/148 |
| 2005/0085691 A1 | * | 4/2005 | Nakao ...................... 600/128 |

FOREIGN PATENT DOCUMENTS

| | | |
|---|---|---|
| WO | WO 98/11825 | 3/1998 |
| WO | WO 2004/112616 A2 | 12/2004 |
| WO | WO 2005/034767 A1 | 4/2005 |

* cited by examiner

*Primary Examiner*—Kevin T Truong
*Assistant Examiner*—Katherine M Dowe
(74) *Attorney, Agent, or Firm*—Brinks Hofer Gilson & Lione

(57) ABSTRACT

An endoscopic cutting device is disclosed. The device comprises an inner catheter including an inner wall having an opening formed therethrough. The inner wall further has a cutting blade moveably disposed thereon and biasingly extends through the opening. The inner wall has a receiving member disposed thereon and is configured to cooperatively receive the cutting blade. The device further comprises an outer catheter including an outer wall moveably disposed about the inner catheter. The outer wall has an aperture formed therethrough. The aperture is configured to moveably align with the opening of the inner wall for allowing the cutting blade to biasingly extend through the opening and biasingly engage the cutting blade with the receiving member to cut.

17 Claims, 3 Drawing Sheets

ENDOSCOPIC CUTTING DEVICE

CROSS-REFERENCE TO RELATED APPLICATIONS

This application claims the benefit of U.S. Provisional Application No. 60/647,517, filed on Jan. 27, 2005, entitled "ENDOSCOPIC CUTTING DEVICE," the entire contents of which are incorporated herein by reference.

BACKGROUND OF THE INVENTION

The present invention relates to endoscopic cutting devices and apparatus for medical procedures involving endoscopic procedures and cutting sutures.

Endoscopic devices have been commonly used for various procedures, typically in the abdominal area. Endoscopy is the examination and inspection of the interior of body organs, joints or cavities through an endoscope. Endoscopy allows physicians to peer through the body's passageways. An endoscopic procedure may be used to diagnose various conditions by close examination of internal organs and body structures, and may also guide therapy and repair, such as the removal of torn cartilage from the bearing surfaces of a joint. A biopsy, a procedure involving tissue sampling for pathologic testing, may also be performed under endoscopic guidance. For example, endoscopic procedures include the following known procedures: gastroscopy, sigmoidoscopy and colonoscopy, esophago gastro duodenoscopy (EGD), endoscopic retrograde cholangiopancreatography (ERCP), and bronchoscopy.

Typically, an endoscope uses two fiber optic lines. A "light fiber" emits light into a body cavity and an "image fiber" carries an image of the body cavity back to a viewing lens. Endoscopes may be used in conjunction with a camera or video recorder to document images of the inside of the joint or chronicle an endoscopic procedure. New endoscopes have digital capabilities for manipulating and enhancing the video images.

An endoscope typically includes at least one separate port to allow for administration of drugs, suction, or irrigation. Such port(s) may also be used to introduce small folding instruments such as forceps, scissors, brushes, snares or baskets for tissue excision, sampling, or other diagnostic and therapeutic work.

For example, endoscopic scissors and forceps may be configured to be used with a particular endoscope for sampling and excision purposes, and for cutting sutures. Although many current endoscopic scissors are adequate, improvements may be made. For instance, current endoscopic scissors typically have a pair of moveable jaws on which blades are disposed. As cuts are made distally from the apex of the jaws, the pressure or cutting effectiveness decreases. As a result, many cuts or dissections are relatively not sharp. When the scissor blades contact sutures (or other items to be cut) adjacent a distal portion of the blades, the results many times involve undesirable shearing.

Thus, it is desirable to provide an improved cutting device compatible with an endoscope.

BRIEF SUMMARY OF THE INVENTION

The present invention generally provides a cutting device that is compatible with an endoscope for endoscopy. The cutting device includes blades that provide effective and relatively sharp dissections along any portion of the blades. The cutting device provides relatively sharp dissections regardless of the cut location along the blade, thereby avoiding shearing and broad cuts. As a result, shearing is avoided.

One embodiment of the present invention provides an endoscopic cutting device. The device comprises an inner catheter including an inner wall having an opening formed therethrough. The inner wall further has a cutting blade moveably disposed thereon and biasingly extending through the opening. The inner wall has a receiving member disposed thereon and is configured to cooperatively receive the cutting blade. The device further comprises an outer catheter including an outer wall moveably disposed about the inner catheter. The outer wall has an aperture formed therethrough. The aperture is configured to moveably align with the opening of the inner wall for allowing the cutting blade to biasingly extend through the opening and biasingly engage the cutting blade with the receiving member to cut.

In another embodiment, the cutting device comprises an inner catheter including an inner wall having a proximal portion and a closed distal portion. The distal portion has an opening formed therethrough. The inner wall further has a spring loaded cutting blade disposed thereon and biasingly extending through the opening. The inner wall has a receiving member disposed thereon and is configured to cooperatively receive the cutting blade.

The cutting device further comprises an outer catheter including an outer wall having a proximal end and an open distal end. The outer wall is slidably disposed about the inner catheter. The outer wall has an aperture formed therethrough. The aperture of the outer wall is configured to align with the opening of the inner wall, allowing the cutting blade to biasingly extend therethrough and biasingly engage the receiving member to cut.

In yet another embodiment, the present invention provides an endoscopic cutting apparatus. The apparatus comprises an inner catheter including an inner wall having a proximal portion and a closed distal portion. The distal portion has an opening formed therethrough. The inner wall further has a spring loaded cutting blade disposed thereon and biasingly extending through the opening. The inner wall has a receiving member disposed thereon and is configured to cooperatively receive the cutting blade.

The apparatus further comprises an outer catheter including an outer wall having a proximal end and an open distal end. The outer wall is slidably disposed about the inner catheter. The outer wall has an aperture formed therethrough. The aperture of the outer wall is configured to align with the opening of the inner wall, allowing the cutting blade to biasingly extend therethrough and biasingly engage the receiving member to cut.

Further objects, features, and advantages of the present invention will become apparent from consideration of the following description and the appended claims when taken in connection with the accompanying drawings.

DETAILED DESCRIPTION OF THE INVENTION

The present invention generally comprises a cutting device that provides relatively sharp dissections regardless of the cut location along its blade, thereby minimizing shearing and broad cuts. The embodiments of the present invention comprise inner and outer catheters having open areas formed therethrough and configured to be aligned. The inner catheter includes a receiving member and a cutting blade that biasingly extends through the open area of the inner catheter. The outer catheter is slidably retractable to force the cutting blade inward and engage the receiving member to cut a suture or dissect a vessel or an organ. As a result, the likelihood of shearing is reduced.

Figure 1:
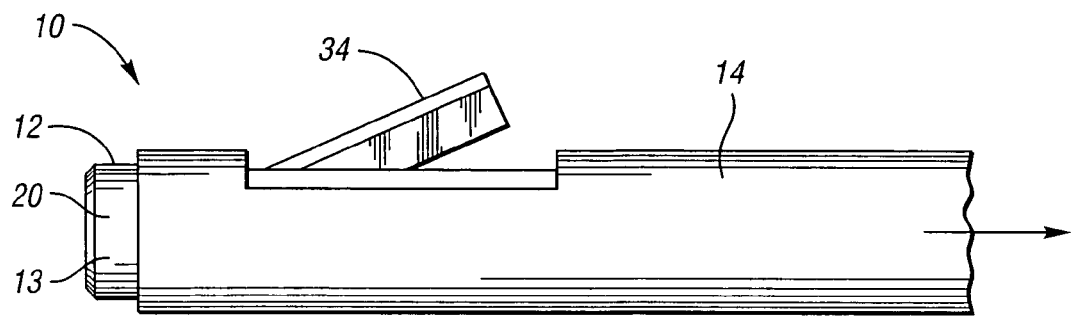
FIG. 1 is a partial side view of an endoscopic cutting device in accordance with one embodiment of the present invention.

FIG. 1 illustrates an endoscopic cutting device 10 in accordance with one embodiment of the present invention. The cutting device 10 is compatible with an endoscope for endoscopy and cutting sutures. For example, the cutting device 10 may be implemented for the following procedures: cutting sutures with an endoscope, gastroscopy, sigmoidoscopy and colonoscopy, esophago gastro duodenoscopy (EGD), endoscopic retrograde cholangiopancreatography (ERCP), and bronchoscopy. The cutting device 10 provides relatively sharp dissections regardless of the cut location along the blade, thereby avoiding shearing and broad cuts.

Figure 2:
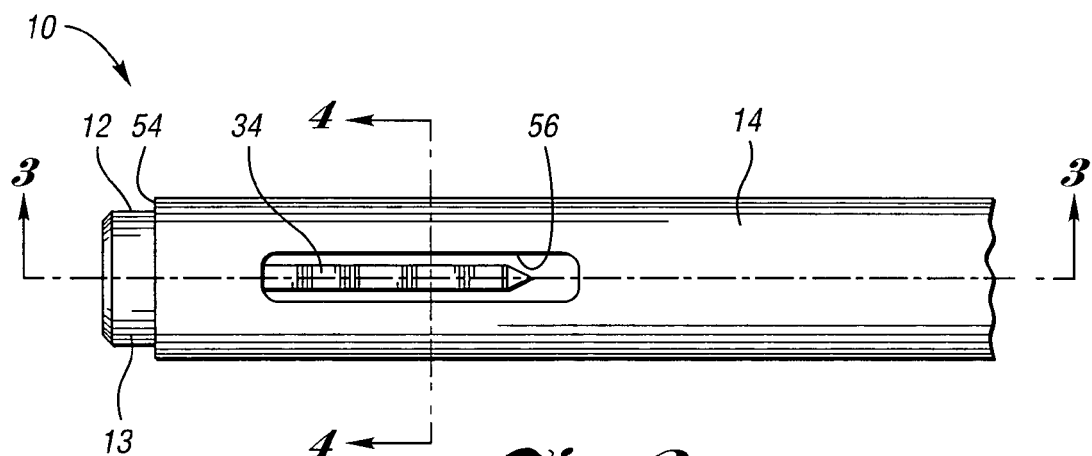
FIG. 2 is another partial side view of the endoscopic cutting device of FIG. 1.
Figure 3:
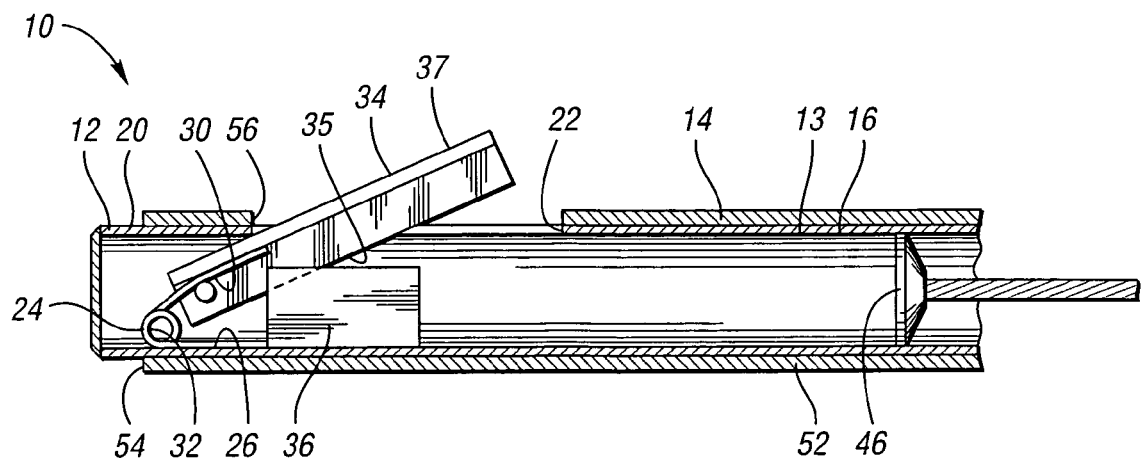
FIG. 3 is a cross-sectional view of the endoscopic cutting device of FIG. 2 taken along line 3-3.

As shown in FIGS. 2 and 3, the cutting device 10 comprises an inner catheter 12 having an inner wall 13 and an outer catheter 14 slidably disposed about the inner catheter 12. Preferably, inner wall 13 has a proximal portion 16 and a closed distal portion 20. The inner catheter 12 may be made of any suitable material such as Nitinol or polymeric materials, e.g., low density polyethylene, polypropylene, polytetrafluoroethylene (PTFE) or mixtures thereof. In this embodiment, the distal portion has a distal opening 22 longitudinally formed therethrough.

Preferably, the inner wall 13 further includes a spring mechanism 24 having first and second arms 26, 30 connected to each other at an apex or a cutting axis 32. The cutting axis 32 is preferably defined by the spring mechanism 24. As shown, the first and second arms 26, 30 are spring-loaded to biasingly extend away from each other relative the apex 32. In this embodiment, the first arm 26 is attached to the inner wall 13 and the second arm 30 biasingly extends proximally from the first arm 26 through the opening 22. Thus, the first arm 26 remains stationary on the inner wall 13 while the second arm 30 is biasingly pivotable relative to the first arm 26. It is to be noted that the spring mechanism 24 may be positioned such that the second arm 30 extends distally relative to the cutting device 10.

As shown, the inner wall 13 further includes a cutting blade 34 attached to the second arm 30 of the spring mechanism 24 adjacent the distal opening 22. In this embodiment, the cutting blade 34 comprises a cutting edge 35 for cutting and a back or non-cutting edge 37 opposite the cutting edge 35. Thus, the cutting blade 34, being spring-loaded by the spring mechanism 24, biasingly extends proximally through the distal opening 22 of the inner wall 13. Moreover, the cutting blade 34 is pivotably moveable about the cutting axis 32 to cut sutures on the cutting edge 35. The cutting blade 34 may be made of any suitable material such as metal or high density polymer.

Figure 4:
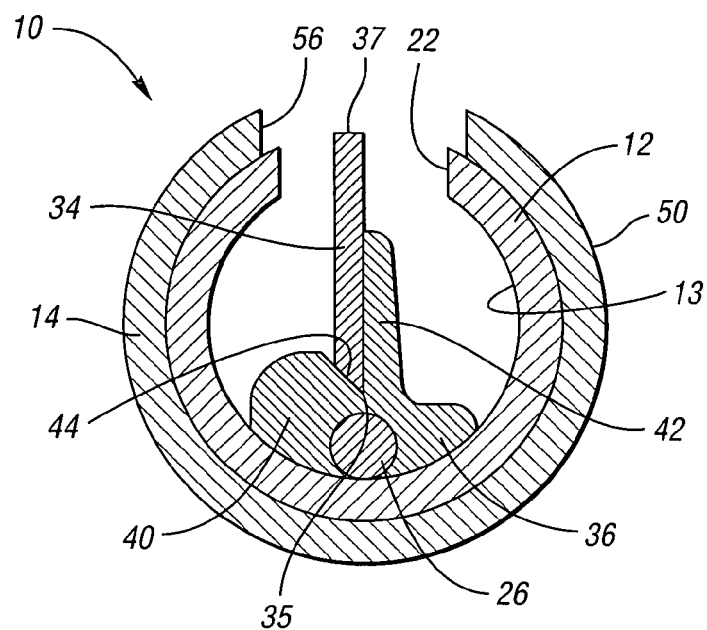
FIG. 4 is another cross-sectional view of the endoscopic cutting device of FIG. 2 taken along line 4-4.

FIGS. 3 and 4 depict the inner wall 13 further including a receiving assembly 36 disposed thereon. In this embodiment, the receiving assembly 36 is disposed on the first arm 26 and is attached to the inner wall 13. As shown, the receiving assembly 36 is configured to cooperatively receive the cutting blade 34 for cutting. The receiving assembly 36 facilitates cutting as the cutting edge 35 of the cutting blade 34 is pivotally moved toward the first arm 30. In this embodiment, the receiving assembly 36 has a base 40 for receiving the cutting edge 35 of the cutting blade 34. As shown, the base 40 is attached on the first arm 26 and extends across a portion of inner catheter 12 to facilitate stability of the spring mechanism 24. The receiving assembly may be made of any suitable material such as metal or high density polymer.

As shown, the receiving assembly 36 further includes a receiving blade 42 extending from the base 40 and is configured to cooperate with the cutting blade 34 for cutting and dissecting. As described in greater detail below, the cutting blade 34 is pivotally moved inwardly to engage with the receiving assembly 36. Cutting and dissecting are achieved by engaging the cutting edge of the cutting blade 34 with the receiving blade 42 to cut suture, vessel, or any other desirable item to be endoscopically cut. The cutting blade 34 is cooperatively received by the base 40 in notch 44.

In this embodiment a drive wire 46 is disposed on the distal portion 20 of the inner wall 13 to position and manipulate the inner wall 13 within the body of a patient. However, other suitable mechanisms may be implemented without falling beyond the scope or spirit of the present invention.

As shown, the cutting device 10 further comprises the outer catheter 14 including an outer wall 50 having a proximal end 52 and an open distal end 54. The outer catheter 14 may be made of any suitable material such as Nitinol or polymeric materials, e.g., low density polyethylene, polypropylene, polytetrafluoroethylene (PTFE) or mixtures thereof. The outer catheter 14 is slidably disposed about the inner catheter 12. The distal end 54 is open to allow clearance for facilitating longitudinal movement of the outer catheter 14 about the inner catheter 12. The outer wall 50 includes an aperture 56 formed therethrough adjacent the distal end 54. The outer wall 50 is configured to slidably move relative to the inner catheter 12 and align the aperture 56 with the distal opening 22 of the inner wall 13.

In this embodiment, retraction of the outer catheter 14 allows engagement between the outer catheter 14 with the back edge 37 of the cutting blade 34, thereby moving the cutting blade 34 downwardly to biasingly engage with the receiving blade 42 for closing the blade and for cutting. The cutting blade 34 is received at the base 40 of the receiving assembly 36. Thus, the force of the outer catheter 14 on the cutting blade 34 is placed directly on an item for cutting, such as a suture. As the outer catheter 14 rides along the cutting blade 34 and forces the cutting blade inwardly, the cutting blade engages the receiving assembly 36 and the item is cut or dissected.

Figure 5:
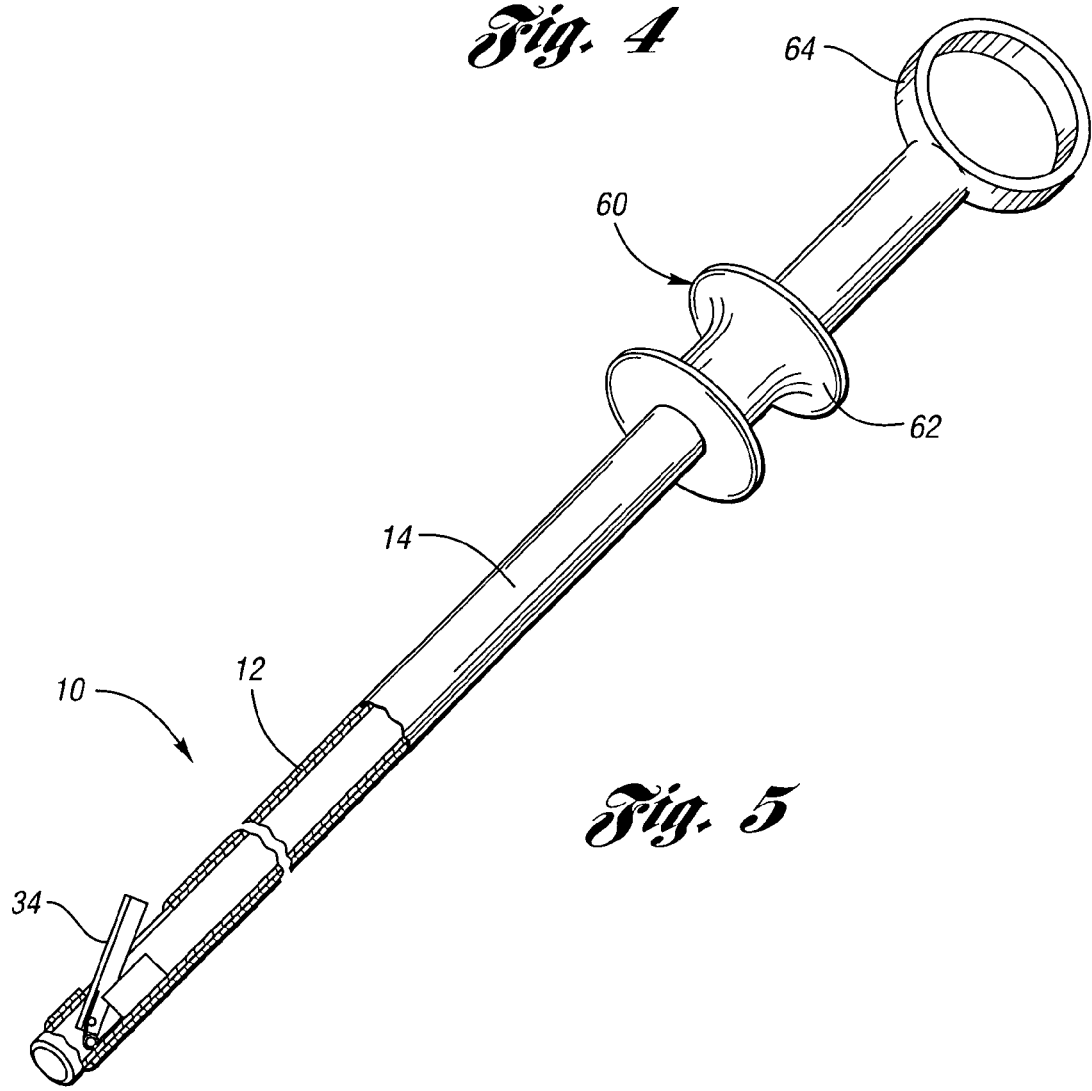
FIG. 5 is a break-away side view of the endoscopic cutting device of FIG. 2.

FIG. 5 illustrates controller 60 cooperable with the drive wire 46 and the inner and outer catheters 12, 14. In this embodiment, the controller 60 includes a spool 62 connected to the drive wire 46 for movement of the inner catheter 12 relative to the outer catheter 14. The controller 60 further includes a handle 64 proximally connected to the outer catheter 14 and configured to facilitate movement thereof for cutting and dissection.

Figure 6:
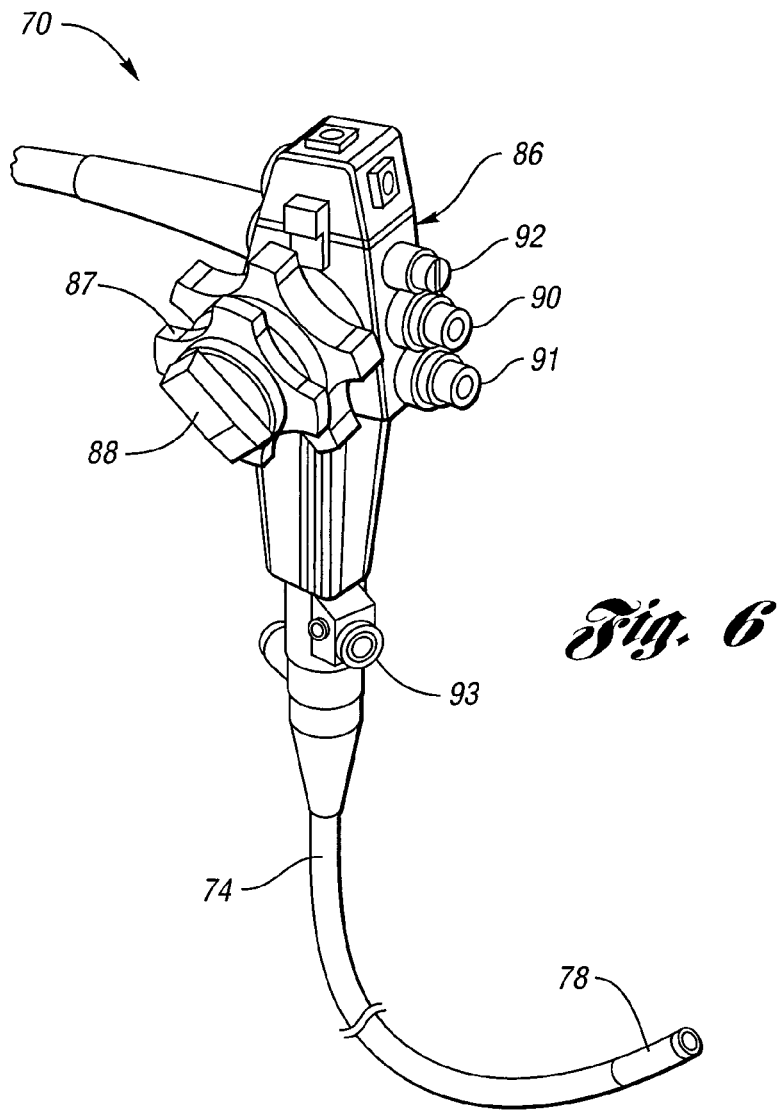
FIG. 6 is an elevated view of an endoscope apparatus implementing the cutting device in accordance with one embodiment of the present invention.
Figure 7:
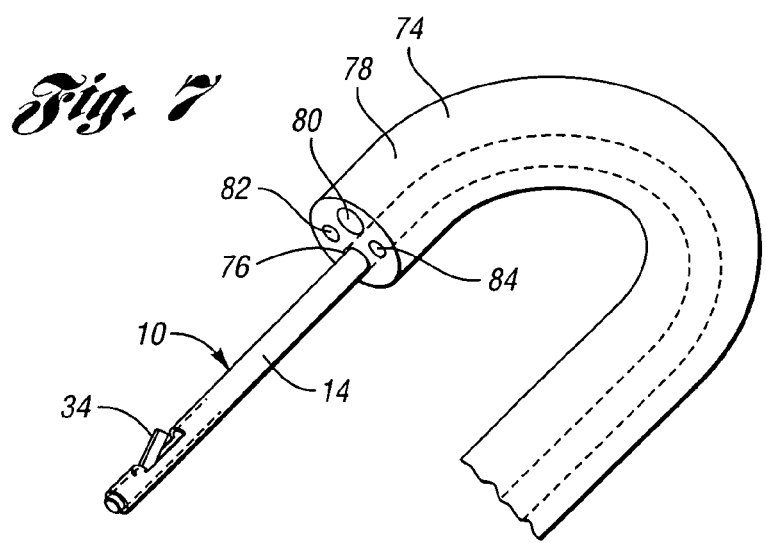
FIG. 7 is a side view of the endoscope apparatus in FIG. 6.

FIGS. 6 and 7 depict an endoscope apparatus 70 having the cutting device 10 in accordance with one embodiment of the present invention. The apparatus 70 may be used for cutting sutures and various other endoscopic procedures including gastroscopy, sigmoidoscopy and colonoscopy, esophago gastro duodenoscopy (EGD), endoscopic retrograde cholangiopancreatography (ERCP), and bronchoscopy. By way of the endoscope apparatus 70, the cutting device 10 provides relatively sharp dissections regardless of the cut location along the blade 34, thereby minimizing shearing and broad cuts.

As shown, the apparatus 70 comprises an endoscopic assembly 72 for endoscopy. The endoscopic assembly 72 includes an insertion tube 74 having a plurality of channel ports 75 through which endoscopic units may be disposed. In one embodiment, the endoscopic units disposed in one of the ports may include one embodiment of the cutting device mentioned above, an endoscopic camera lens 80, a suction source 82, and a water/air flush 84. Other suitable units may be used as desired.

As shown, the endoscopic assembly 72 further includes a control system 86 that is in mechanical and fluid communication with the insertion tube 74. The control system 86 is configured to control the insertion tube 74 and endoscopic parts disposed therein. As shown, the control system 86 includes first and second control knobs 87, 88. The control knobs 87, 88 are configured to be in mechanical communication with the insertion tube 74. The control knobs 87, 88 allow the physician to control and guide, by known means, the insertion tube 74 through vessels and cavities of a patient. The control system 86 further includes valve switches (e.g., suction valve 90, air/water valve 91, camera valve 92), each of which are in communication to one of the channel ports 75 of the insertion tube 74. For example, the suction valve switch 90, when activated, allows a vacuum from a suction source through a suction channel port 82 for suctioning unwanted plaque and debris from the patient.

As shown in FIGS. 6 and 7, the endoscopic apparatus 70 includes the endoscopic cutting device 10 described above. In this embodiment, the endoscopic cutting device 10 is inserted through the biopsy/scissors channel port 76 of the endoscopic assembly 72. The device 10 is then fed through the respective biopsy channel port 76 of the endoscopic assembly 72. The cutting device 10 is preferably fed therethrough until the distal end 54 of the outer catheter 14 is adjacent nozzle 78 of the insertion tube 74.

As mentioned above, the endoscopic cutting device 10 comprises the inner catheter 12 having the cutting base 40 disposed thereon, the outer catheter 14 disposed about the inner catheter 12, and the drive wire 46 attached within the inner catheter 12.

In one example, the distal end of the insertion tube 74 is inserted, rectally or orally, to a predetermined endoscopic location within a patient. Insertion of the insertion tube 74 may be rectally or orally depending on the endoscopic procedure. At the location, a physician may activate and control the endoscopic units as desired, such as to cut sutures previously surgically placed in a patient. The endoscope in combination with the cutting device of the present invention allows the physician to make sharp dissections and cuts as desired.

While the present invention has been described in terms of preferred embodiments, it will be understood, of course, that the invention is not limited thereto since modifications may be made to those skilled in the art, particularly in light of the foregoing teachings.

The invention claimed is:

1. An endoscopic cutting device comprising:
   an inner catheter including an inner wall having a distal opening formed longitudinally through the side of the inner wall, the inner wall further having a cutting blade moveably disposed thereon and biasingly extending through the opening, the cutting blade including a first cutting edge, the inner wall having a receiving member disposed thereon, the receiving member including a receiving blade having a second cutting edge, the receiving member being configured to cooperatively receive the cutting blade, wherein the first cutting edge engagingly contacts the second cutting edge to cut; and
   an outer catheter including an outer wall having a proximal end and an open distal end, the open distal end being open to allow clearance for facilitating longitudinal movement of the outer catheter relative to the inner catheter, the outer wall being moveably disposed about the inner catheter, the outer wall having an aperture formed longitudinally through the side of the outer wall, the aperture being separate from the open distal end and formed proximal to the open distal end through the outer wall, the aperture of the outer wall being configured to moveably align with the distal opening of the inner wall for allowing the cutting blade to biasingly extend through the distal opening, the outer catheter being slidably retractable relative to the inner catheter to force the first cutting edge of the cutting blade inward and biasingly engage the second cutting edge of the receiving blade to cut.

2. The cutting device of claim 1 wherein the inner wall has a proximal portion and a distal portion, the opening being formed through the distal portion.

3. The cutting device of claim 2 wherein the distal portion has a closed distal end.

4. The cutting device of claim 2 further comprising a drive wire disposed on the distal portion of the inner wall for positioning the inner wall within the body of the patient.

5. The cutting device of claim 1 wherein the cutting blade is spring loaded to biasingly extend from the inner wall.

6. The cutting device of claim 1 wherein the receiving member is a receiving assembly having a base for receiving the cutting blade, wherein the receiving blade extends from the base to define a notch for receiving the cutting blade, the second cutting edge of the receiving blade being configured to cooperate with the first cutting edge of the cutting blade for cutting as the cutting blade is cooperatively received in the notch.

7. The cutting device of claim 6 wherein the inner wall further includes:
   a spring mechanism having first and second arms, the first arm being attached to the inner wall and the second arm biasingly extending from the first arm and through the opening, the second arm biasingly moveable relative to the first arm, the receiving assembly being disposed on the first arm and attached to the inner wall, the cutting blade being disposed on the second arm and being moveable for cutting.

8. The cutting device of claim 7 wherein the second arm is biasingly pivotable about a cutting axis of the cutting blade, the cutting axis being defined by the spring.

9. The cutting device of claim 1 wherein the cutting blade comprises a back edge opposite the cutting edge.

10. An endoscope apparatus having a cutting apparatus, the apparatus comprising:
    an endoscopic assembly for endoscopy, the assembly comprising:
       an insertion tube, the insertion tube having a plurality of channels through which endoscopic parts may be disposed; and a control system in mechanical and fluid communication with the insertion tube, the control system being configured to control at least one of the endoscopic parts; and an endoscopic cutting device disposed in one of the plurality of channels of the endoscopic assembly, the endoscopic cutting device comprising:

an inner catheter including an inner wall having a proximal portion, a closed distal portion, and an opening formed longitudinally through a side of the inner wall adjacent the distal portion, the inner wall further having a spring loaded cutting blade disposed thereon and biasingly extending through the opening, the cutting blade including a first cutting edge, the inner wall having a receiving member disposed thereon, the receiving member including a receiving blade having a second cutting edge, the receiving member being configured to cooperatively receive the cutting blade, wherein the first cutting edge engagingly contacts the second cutting edge to cut; and an outer catheter including an outer wall having a proximal end and an open distal end, the outer wall being slidably disposed about the inner catheter, the outer wall having an aperture formed therethrough, the aperture of the outer wall being configured to align with the opening of the inner wall, allowing the cutting blade to biasingly extend therethrough and biasingly engage the receiving member to cut, wherein the receiving member has a base for receiving the cutting blade, the receiving blade extending from the base to define a notch to receive the cutting blade, the second cutting edge of the receiving blade being configured to cooperate with the first cutting edge of the cutting blade for cutting as the cutting blade is cooperatively received in the notch.

11. The apparatus of claim 10 further comprising a drive wire disposed on the distal portion of the inner wall for positioning the inner catheter within the body of the patient.

12. The apparatus of claim 11 further comprising a handle assembly cooperable with the drive wire, the handle assembly including a spool disposed about the drive wire for movement of the drive wire therethrough and a handle proximally connected to the drive wire for facilitating movement of the drive wire while positioning the inner catheter within the body of the patient.

13. The apparatus of claim 10 wherein the inner wall of the device further includes:

a spring mechanism having first and second arms, the first arm being attached to the inner wall and the second arm biasingly extending from the first and through the opening, the second arm biasingly moveable relative to the first arm, the receiving assembly being disposed on the first arm and attached to the inner wall, the cutting blade being disposed on the second arm and being moveable for cutting.

14. The apparatus of claim 13 wherein the second arm of the device is biasingly pivotable about a cutting axis of the cutting blade, the cutting axis being defined by the spring mechanism.

15. The apparatus of claim 10 wherein the cutting blade of the device comprises a back edge opposite the cutting edge.

16. The apparatus of claim 15 wherein the outer catheter engages the back edge of the cutting blade to move the cutting blade downwardly to biasingly engage with the receiving blade for closing the blade and cutting.

17. An endoscopic cutting device comprising:

an inner catheter including an inner wall having a distal opening formed longitudinally through the side of the inner wall, the inner wall further having a cutting blade moveably disposed thereon and biasingly extending through the opening, the cutting blade including a first cutting edge, the inner wall having a receiving member disposed thereon, the receiving member including a base for receiving the cutting blade, the receiving member further including a receiving blade having a second cutting edge, the receiving blade extending from the base to define a notch to receive the cutting blade, the receiving member being configured to cooperatively receive the cutting blade, wherein the first cutting edge engagingly contacts the second cutting edge to cut as the cutting blade is received in the notch; and an outer catheter including an outer wall having a proximal end and an open distal end, the open distal end being open to allow clearance for facilitating longitudinal movement of the outer catheter relative to the inner catheter, the outer wall being moveably disposed about the inner catheter, the outer wall having an aperture formed longitudinally through the side of the outer wall, the aperture being separate from the open distal end and formed proximal to the open distal end through the outer wall, the aperture of the outer wall being configured to moveably align with the distal opening of the inner wall for allowing the cutting blade to biasingly extend through the distal opening, the outer catheter being slidably retractable relative to the inner catheter to force the first cutting edge of the cutting blade inward and biasingly engage the second cutting edge of the receiving blade to cut.

* * * * *